United States Patent [19]

Schnepp-Pesch et al.

[11] Patent Number: 4,998,919
[45] Date of Patent: Mar. 12, 1991

[54] THROMBECTOMY APPARATUS

[76] Inventors: Wolfram Schnepp-Pesch, Schönblick 6, 7505 Ettlingen; Josef Lindenberg, Käthe-Kollwitz-Str.10a, 7500 Karlsruhe, both of Fed. Rep. of Germany

[21] Appl. No.: 259,301

[22] Filed: Oct. 18, 1988

[30] Foreign Application Priority Data

Oct. 31, 1987 [DE] Fed. Rep. of Germany ... 8714529[U]

[51] Int. Cl.$^5$ ............................................. A61M 25/01
[52] U.S. Cl. ..................................... 604/164; 604/264; 604/280; 128/657
[58] Field of Search ....................... 604/52, 53, 93, 95, 604/164, 280, 264; 128/348.1, 657, 658

[56] References Cited

U.S. PATENT DOCUMENTS

| | | | |
|---|---|---|---|
| 4,033,331 | 7/1977 | guss et al. | 128/657 |
| 4,601,713 | 7/1986 | Fuqua | 604/96 |
| 4,686,984 | 8/1987 | Bonnet | 604/264 X |
| 4,769,005 | 9/1988 | Ginnsburg et al. | 604/164 X |

FOREIGN PATENT DOCUMENTS 2565491 12/1985 France .................... 604/284

Primary Examiner—Stephen C. Pellegrino
Attorney, Agent, or Firm—Antonelli, Terry, Stout & Kraus

[57] ABSTRACT

A method and apparatus for thrombectomy with partial dissolving by streptokinase or the like, wherein a catheter set with a sheath having two open lumens extending in parallel over most of the length of the sheath. The lumen are distal-parallel to one another and issue proximally under a finite angular alignment. The first lumen takes up virtually the entire cross-sectional area of sheath, while the second lumen is much narrower and is constructed in a widened area of the wall of the first lumen. A safety change wire is adapted to be accommodated in the second lumen.

16 Claims, 2 Drawing Sheets

THROMBECTOMY APPARATUS

BACKGROUND OF THE INVENTION

The present invention relates to a thrombectomy apparatus and method for partially dissolving of thrombus by a thrombus dissolving liquid such as, for example, streptokinase or the like.

Thrombectomy apparatuses of this type are known and have a guide wire and a catheter guidable via the same having a distal and a proximal open lumen having a proximal-connectable infusion and/or suction syringe. The procedure adopted in this known apparatus is that initially the guide wire is passed through the tissue of the patient into a vein and along the latter to a thrombus to be removed. Subsequently the catheter is passed via the guide wire to the thrombus, the guide wire is removed, optionally through the catheter is injected an agent, such as streptokinase which wholly or partly dissolves the thrombus and finally the thrombus parts are removed by suction. It can arise that the thrombus parts stick and all the parts introduced into the vein must be removed with a thrombus part from the body. The hole procedure must then be repeated with puncture and controlled, X-ray-observed introduction of the guide wire, which is prejudicial to the patient.

A catheter not of the present type for destroying blood vessel blockages by laser energy is known, which is introduced by its lumen via a guide wire and through lumen cooling and washing liquid can be injected. An optical fibre is embedded in the wall through which the laser energy can be passed to the distal end of the catheter. In addition, double lumen balloon catheters are known, in which a second lumen in the side wall of the catheter issues radially under an elastic film inflatable as a balloon and fixed around the catheter.

SUMMARY OF THE INVENTION

The aim underlying the present invention essentially resides in providing an apparatus of the aforementioned type and method for a thrombectomy by partial dissolving and sucking away of a thrombus material which reduces stressing of the patient and permits a greater variation possibility with respect to thrombus removal.

According to the invention, in the case of an apparatus of the aforementioned type, the aim of the invention is achieved by a catheter set with a double lumen sheath with two lumens open at both sides and extending in parallel over most of the length of the sheath, which are distal-parallel to one another and issue proximally under a finite angular alignment, with the first lumen taking up virtually the entire cross-sectional area of the sheath, whereas, the second lumen is much narrower and is formed in the wall of the first lumen, while there is a safety change wire adapted to the second lumen.

The invention apparatus makes it possible to remove the complete sheath, including optionally a catheter inserted therein from the body of the patient in the case of sucked in thrombus parts. The safety change wire is left behind and the in an easy manner and without a renewed complete puncture and introduction controlled under X-ray-observation being necessary, the sheath or a new sheath can be a again introduced to the thrombus. According to a preferred development of the invention there is a first catheter adapted to the cross-section of the first lumen. In this case, the sheath wall can be extremely thin, because it no longer need have any inherent stiffness and instead this is optionally ensured by the catheter. A further development of the inventive apparatus is characterized by a guide wire adapted to the sheath and/or the first catheter in such a way that introduction thereof is possible by means of it and also by a puncture cannula adapted to the guide wire with its lumen. As a result of this set-like construction of the inventive apparatus it is ensured that the surgeon has suitable, adapted parts, puncture cannula and guide wire, which are matched with other parts of the inventive apparatus and in particular the catheter set and can be used in an optimum manner. There is at least one syringe for injecting a thrombus-dissolving liquid, such as streptokinase and/or for sucking off the thrombus material. The syringes are provided with adaptors in such a way that they can be readily attached to the corresponding adaptor of the sheath and/or the catheter, particularly through a bayonet-like adaptor construction. In an injection syringe is provided, this can be filled with a thrombus-dissolving agent, such as streptokinase, so that it is immediately ready for use and there is no need to additionally draw up the streptokinase. According to a preferred construction in this case the adaptor of the syringe has a closed end, which can be cut off, so as to permit the injection of the liquid by the resulting opening.

According to a further preferred construction, the first catheter has a narrowly drawn out, tapering distal tip. A second catheter is constructed with a wide, open distal end corresponding to the lumen cross-section over its entire length. The catheter with the tapering distal end facilitates the introduction of the catheter set up to the thrombus, while the catheter with a wide, open distal end makes it possible to suck larger thrombus parts through the catheter than would be possible with a catheter having a tapering end. So that in the case of the given external diameter of the sheath of approximately 11 to 12 Charrière (Ch), there is a maximum internal diameter for the catheter and to enable large thrombus parts to be sucked through, apart from the airlock wall thickness, which is preferably approximately 0.2 mm or in particular below this value, the internal diameter of the second lumen of the sheath and therefore the cross-section of the safety change wire should be as small as possible, particularly below 0.5 mm and especially advantageously below 0.2 mm, i.e. of the same order of magnitude as the thin wall of the sheath. Thus, in the case of an sheath with the above-mentioned external diameter, there is a large lumen internal diameter of approximately 8 to 10 Charrière in the case of acceptable external dimensions.

BRIEF DESCRIPTION OF THE DRAWINGS

The invention is described in greater detail hereinafter relative to a non-limitative embodiment of the invention and with reference to the attached drawings, wherein.

DETAILED DESCRIPTION OF THE INVENTION

Figure 1:
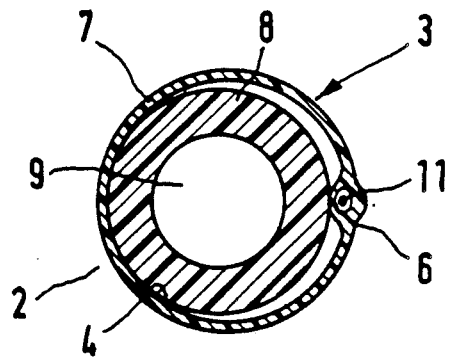
FIG. 1 is a cross-sectional view of a catheter set constructed in accordance with the present invention.

The inventive apparatus 1 has a catheter set generally designated by the reference numeral 2 with a sheath generally designated by the reference numeral 3, with a first lumen 4 and a second lumen 6. The first lumen 4 has a cross-section which virtually fills the entire cross-section of the sheath 3 and is e.g. approximately 3.5 mm in the case of an external diameter of approximately 3.8 mm. The second lumen 6 is constructed in the wall 7 of the sheath 3 and has a much smaller cross-section with a diameter of approximately 0.6 mm. As can be gathered from what has been stated hereinbefore, the sheath wall 7 is extremely thin and therefore highly flexible. Its wall thickness is approximately 0.1 to 0.2 mm. A catheter 8 is inserted in the sheath 3, so that the complete unit with the lumen 9 of the catheter 8 can be introduced via a guide wire. A safety change wire 11 is located in the second lumen of sheath 3. Streptokinase can now be injected by a syringe through the lumen 9 of the catheter 8. Thrombus parts can now be sucked by a vacuum syringe through the catheter lumen 9, so that together with the catheter 8 they are sucked through the first lumen 4 of sheath 3 or can be drawn out together with the sheath 3 leaving the safety change wire 11 behind. Optionally, with the catheter 8 removed, suction takes place directly through the sheath 3 if the airlock has an adequate inherent stability. The decision to be made here is generally between the thinnest possible wall and an adequate inherent stability also with respect to suction pressure.

Figure 2A:
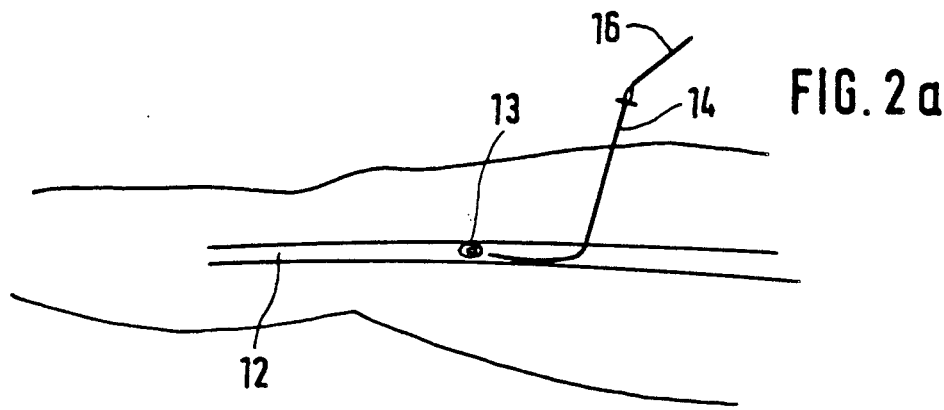
FIGS. 2a–2e are schematic side views illustrating different steps in utilizing the catheter set constructed in accordance with the present invention.
Figure 2B:
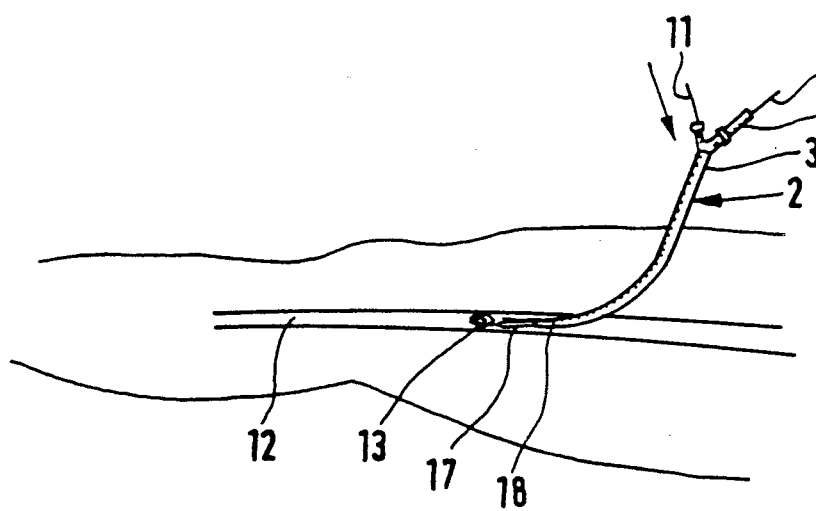
Figure 2C:
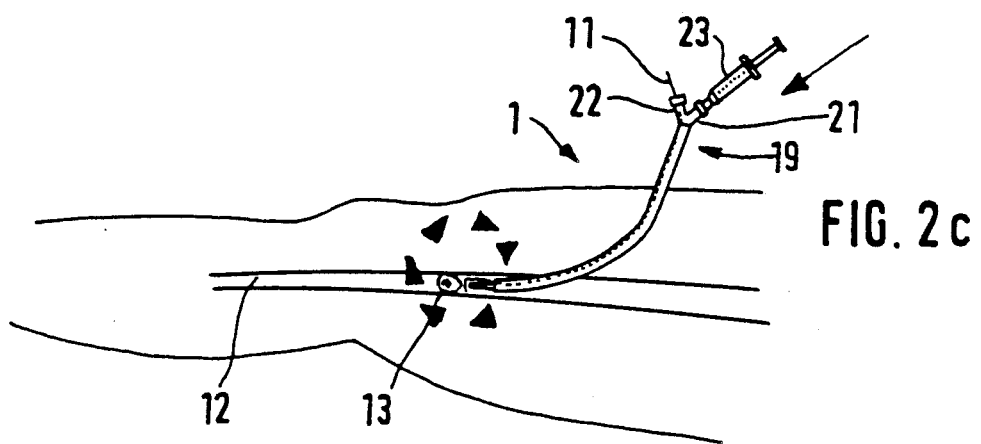
Figure 2D:
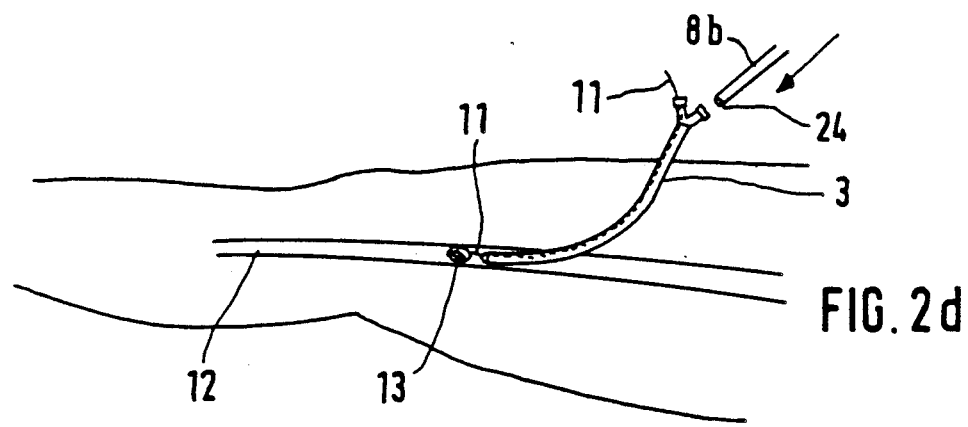
Figure 2E:
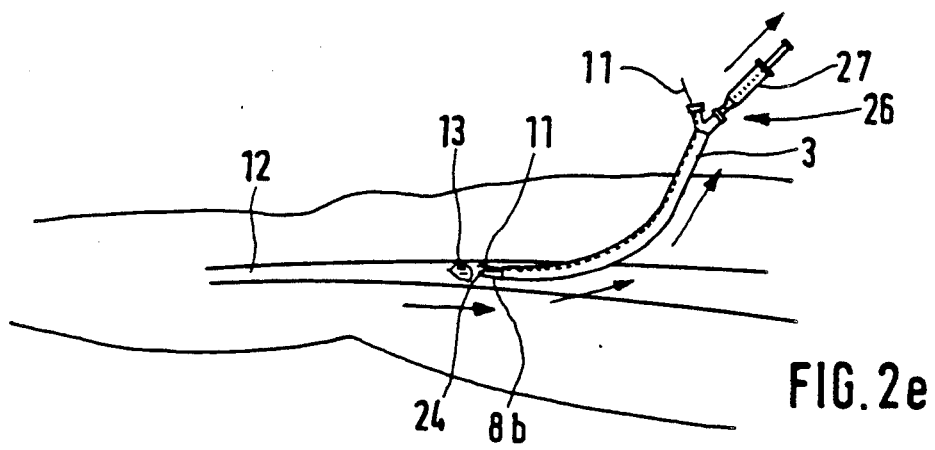

As shown in FIGS. 2a–2e, in use, the vein 12 of a patient is punctured by a puncture cannula 14, such as a Seldinger Puncture Cannula close to a thrombus 13. A guide wire 16 is then introduced through the puncture cannula 14 close to the thrombus 13. In the next stage the puncture cannula 14 is drawn out via the guide wire 16, which stays behind. The catheter set 2 with in particular the sheath 3, and preferably with the catheter 8a in its larger lumen 4 and the safety change wire 11 located in the smaller cross-section, and the second lumen 6 are introduced by the guide wire 16 into the vein 12 and also close to the thrombus 13. Optionally the safety change wire 11 can be inserted through the second lumen 6 after the introduction of sheath 3.

The catheter 8a is preferably a so-called Van-Andel catheter, which has a pointed distal end 17 and a greater length than the sheath 3, so that its distal end 17 projects over the distal end 18 of the sheath 3. As a result of the construction of the Van-Andel catheter 8a, the insertion of the catheter set is facilitated. Guide wire 16 is then removed from the lumen 9 of catheter 8a.

At their proximal ends, sheath 3 and/or catheter 8a have, in an area 19, adaptors 21,22, such as Luer Adaptors. For this purpose the proximal openings of lumens 4,6 of air-lock 3, which are otherwise parallel to one another over the entire length of sheath 3, are directed away from one another under a finite angle, so that manipulations can take place in a free and undisturbed manner at both lumen openings. The angle between the proximal lumen openings is greater than 30° and, preferably, between 45° and 90°, the two openings enclosing roughly the same angle with respect to the axis of the residual sheath 3. A streptokinase-filled injection syringe 23 can now be fitted to an adaptor 21 and, as a result, streptokinase can be injected into vein 12 into the vicinity of thrombus 13. In known manner, the streptokinase brings about a partial dissolving of the thrombus 13, so that the thrombus 13, which was previously fixed in vein 12 is dissolved or at least parts thereof are dissolved.

In a particularly preferred manner, the Van-Andel catheter 8a is drawn out of the sheath 3 and a further catheter 8b is introduced through the sheath to thrombus 13. Catheter 8b differs from the Van-Andel catheter 8a through a larger distal opening 24 enabling larger parts of the thrombus 13 to be sucked up to the opening 24.

At the proximal end 26 of suction catheter 8b, a suction syringe 27 is fitted to an adaptor located there and this enables thrombus parts to be sucked through the catheter 8b or onto the opening 24 of catheter 8b.

To the extent that the thrombus parts have smaller external dimensions than the internal diameter of airlock 3, even if they are located at the opening 24 of catheter 8b, they can be drawn out of the latter through sheath 3 out of the patient's body and then removed. As for shortening the removal of the thrombus and for reducing patient stress, attempts are made to move maximum size thrombus parts, it may occur that such a part may stick in the vicinity of the distal opening of the sheath 3 or in the latter, so that the complete sheath 3 has to be removed from the patient's body. It is then drawn out via the safety change wire 11 with the thrombus part, with the wire 11 remaining in the body with its distal end close to the thrombus 13. By means of and along the safety wire 11 the same or a new catheter set can be introduced to the thrombus, as was described hereinbefore and the removal of the thrombus can be continued by partial dissolving by streptokinase and suction removal of thrombus parts. Alternating infusion/suction is continued until the thrombus has been completely removed.

The inventive apparatus offers great variability with respect to thrombus removal. Thus, as stated, the sheath 3 can have an appropriate inherent stiffness to enable suction to take place directly through the sheath 3 in the case of large thrombus fragments. For the complete duration of surgery, the safety change wire 11 located in the second lumen 6 of the airlock provides a guide rail, which also brings about stability in the axial direction. Optionally for the suction of also the Van-Andel catheter, or for introduction and injection it is possible to use a catheter 8b with a larger distal opening. Moreover, streptokinase can be injected through the second, smaller cross-section lumen 6, while simultaneously thrombus parts are sucked through the first lumen 4.

What is claimed is:

1. An apparatus for thrombectomy with partial dissolving of a thrombus by a thrombus dissolving liquid, the apparatus comprising sheath means having at least first and second open lumens extending over an entire length of the sheath means, said first and second lumens each including proximal and distal ends, said first and second lumens are distal-parallel to one another and disposed parallel to one another over most of the length of the sheath means, the proximal ends of said first and second lumens subtend a finite angle, said first lumen has a cross-sectional area taking up virtually an entire cross-sectional area of sheath means, said second lumen has a cross-sectional area narrower than the cross-sectional area of said first lumen and is located in a widened area of a wall of said sheath means, said cross-sectional areas of said first and second lumens are substantially constant over an entire length of the parallel disposed portions thereof, said second lumen is adapted to accommodate a safety change wire means, and wherein at least one first catheter means is provided, said first catheter means being dimensioned so as to be accommodated in said first lumen.

2. An apparatus according to claim 1, further comprising a guide wire means adapted to be accommodated in at least one of the sheath means and said first catheter means so as to permit an introduction of the guide wire means therein.

3. An apparatus according to one of claims 1 or 2, further comprising at least one syringe means for at least one of injecting the thrombus-dissolving liquid and for drawing off dissolved thrombus material.

4. An apparatus according to claim 3, wherein the catheter means includes a narrow, drawn-out, tapering distal tip.

5. An apparatus according to claim 4, further comprising a second catheter means having at a distal end thereof a wide opening with a cross-section substantially corresponding to a cross-section of a lumen of the second catheter means over an entire length thereof so as to enable said second catheter means to draw larger thrombus parts therethrough than the thrombus parts drawn into the first catheter means.

6. An apparatus according to one of claims 1 or 2, wherein the sheath means has a wall thickness of less than 0.2 mm.

7. An apparatus according to one of claims 1 or 2, wherein an internal diameter of said first lumen of said sheath means is between 8 and 12 Charriere.

8. An apparatus according to claim 7, wherein an external diameter of said sheath means is approximately 11 to 12 Charriere.

9. An apparatus according to claim 8, wherein an internal diameter of said second lumen of said sheath means is less than 0.7 mm.

10. An apparatus for thrombectomy with partial dissolving of a thrombus by a thrombus dissolving liquid, the apparatus comprising sheath means having at least first and second open lumens extending over an entire length of the sheath means, said first and second lumens each including proximal and distal ends, said first and second lumens are distal-parallel to one another and disposed parallel to one another over most of the length of the sheath means, the proximal ends of said first and second lumens subtend a finite angle, said first lumen has a cross-sectional area taking up virtually an entire cross-sectional area of said sheath means, said second lumen has a cross-sectional area narrower than the cross-sectional area of said first lumen and is located in a widened area of a wall of said sheath means, said cross-sectional areas of said first and second lumens are substantially constant over an entire length of the parallel disposed portions thereof, said second lumen is adapted to accommodate a safety change wire means, and said sheath means has a wall thickness of less than 0.2 mm.

11. An apparatus according to claim 10, wherein an internal diameter of said first lumen of said sheath means is between 8 and 12 Charriere.

12. An apparatus according to one of claims 10 or 11, wherein an external diameter of said sheath means is approximately 11 to 12 Charriere.

13. An apparatus according to claim 12, wherein an internal diameter of said second lumen of said sheath means is less than 0.7 mm.

14. An apparatus for thrombectomy with partial dissolving a thrombus by a thrombus dissolving liquid, the apparatus comprising sheath means having at least first and second open lumens extending over an entire length of the sheath means, said first and second lumens each including proximal and distal ends, said first and second lumens are distal-parallel to one another and disposed parallel to one another over most of the length of the sheath mans, the proximal ends of said first and second lumens subtend a finite angle, said first lumen has a cross-sectional area taking up virtually an entire cross-sectional area of said sheath means, said second lumen has a cross-sectional area narrower than the cross-sectional area of said first lumen and is located in a widened area of a wall of said sheath means, said cross-sectional areas of said first and second lumens are substantially constant over an entire length of the parallel disposed portions thereof, said second lumen is adapted to accommodate a safety change wire means, wherein an internal diameter of said first lumen of said sheath means is between 8 and 12 Charriere.

15. An apparatus according to claim 14, wherein an external diameter of said sheath means is approximately 11-12 Charriere.

16. An apparatus according to one of claims 14 or 15 wherein an internal diameter of said second lumen of said sheath means is less than 0.7 mm.

* * * * *